United States Patent [19]

Albal et al.

[11] Patent Number: 4,994,625
[45] Date of Patent: Feb. 19, 1991

[54] PRODUCTION OF HYDROGEN PEROXIDE

[75] Inventors: Rajendra S. Albal; Robert N. Cochran, both of West Chester, Pa.

[73] Assignee: Arco Chemical Technology, Inc., Wilmington, Del.

[21] Appl. No.: 457,605

[22] Filed: Dec. 27, 1989

[51] Int. Cl.$^5$ .................. C07C 27/00; C07C 45/00
[52] U.S. Cl. .................. 568/311; 423/591; 568/815
[58] Field of Search ............ 423/584, 591; 568/311, 568/815

[56] References Cited

U.S. PATENT DOCUMENTS

| 3,410,659 | 11/1968 | Muehlhausser | 23/293 R |
|---|---|---|---|
| 3,928,452 | 12/1975 | Brunie et al. | 568/311 |
| 3,968,162 | 7/1976 | Lartigau et al. | 568/311 |
| 4,508,923 | 4/1985 | Taylor | 568/311 |

FOREIGN PATENT DOCUMENTS 2435  1/1978  Japan .................. 568/815

Primary Examiner—Wayne A. Langel
Attorney, Agent, or Firm—William C. Long

[57] ABSTRACT

Hydrogen peroxide and organic active oxygen-containing compounds in an organic stream, such as that from a methyl benzyl alcohol oxidate after hydrogen peroxide separation, are selectively decomposed by contact with an alumina catalyst, the organic active oxygen materials selectively decomposing to acetophenone and methyl benzyl alcohol.

3 Claims, 1 Drawing Sheet

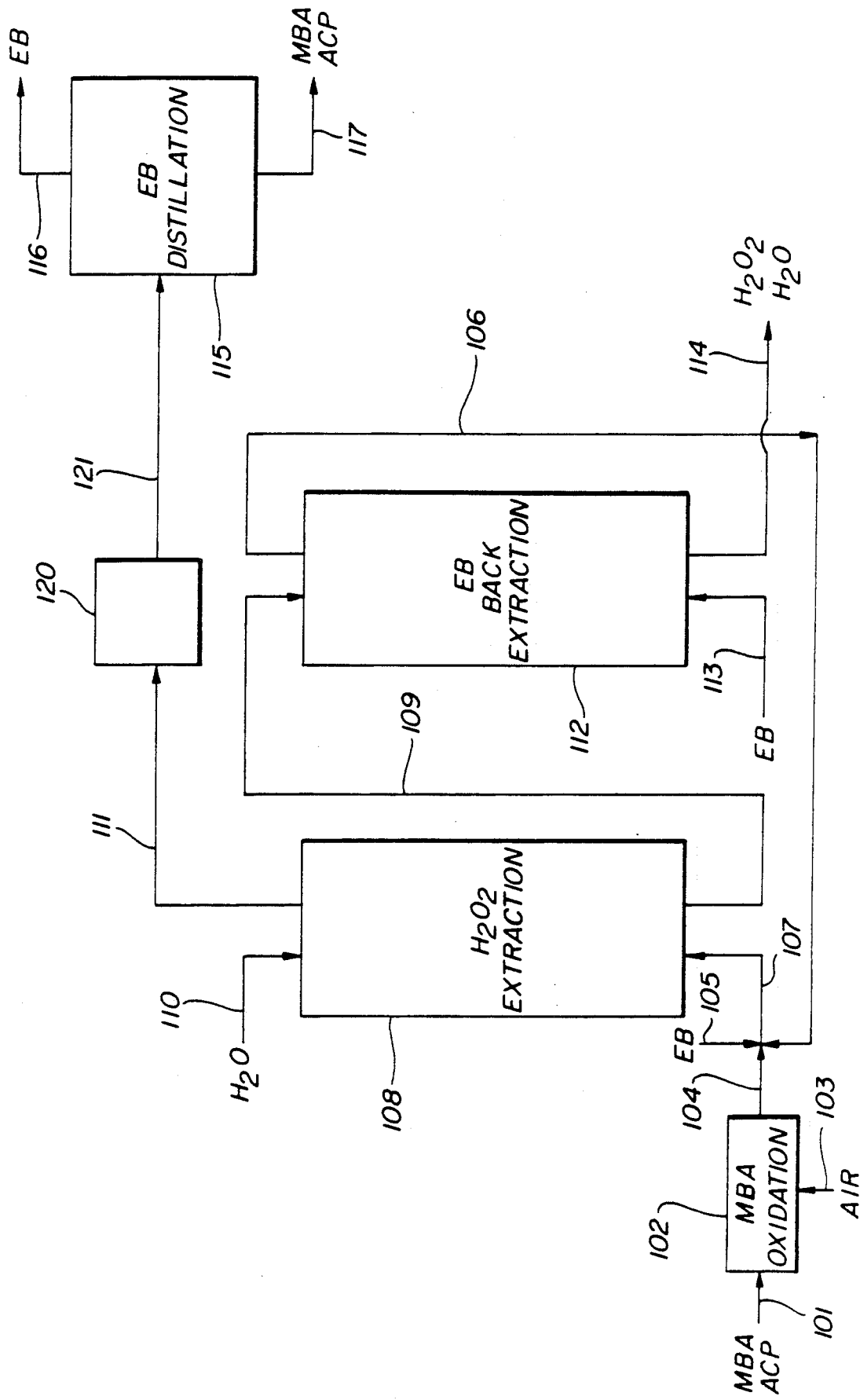

4,994,625

PRODUCTION OF HYDROGEN PEROXIDE

BACKGROUND OF THE INVENTION

1. Field of the Invention

The present invention relates to the production of hydrogen peroxide by the oxidation of methyl benzyl alcohol.

2. Description of the Prior Art

Hydrogen peroxide is an important chemical of commerce which is produced in very large quantities for use in a number of industrial applications. The predominant process used commercially for the production of hydrogen peroxide involves the oxidation of anthrahydroquinone, extraction of hydrogen peroxide and reduction of the resulting anthraquinone to anthrahydroquinone which is reused. This process requires very high capital expenditures in that use of a working solvent with efficient recycle of various process components is necessary.

Substantial efforts have been directed to processes which involve direct combination of hydrogen and oxygen but thus far such processes have not found widespread success.

Hydrogen peroxide has been formed by the oxidation of secondary alcohols. At one time the production of hydrogen peroxide by oxidation of isopropanol was practiced commercially. Other secondary alcohols which have been mentioned as possible starting materials for hydrogen peroxide production include methyl benzyl alcohol and cyclohexanol. See, for example, U.S. Pat. Nos. 2,871,102-4 of Shell Development.

Hydrogen peroxide has also been formed by oxidation of high boiling secondary alcohols such as diaryl methanol, the product hydrogen peroxide being stripped from the reaction mixture during oxidation; see U.S. Pat. No. 4,303,632.

In certain commercial technologies substantial quantities of various secondary alcohols are produced. For example, in the coproduction of propylene oxide and styrene monomer by hydroperoxide epoxidation, methyl benzyl alcohol which is also referred to as alpha phenyl ethanol, 1-phenyl ethanol or methyl phenyl carbinol, is formed and ultimately converted by dehydration to styrene monomer. See U.S. Pat. No. 3,351,635.

An improved process for the production of hydrogen peroxide by the oxidation of methyl benzyl alcohol is described in copending U.S. application Ser. No. 07/295,409 filed Jan. 10, 1989, U.S. Pat. No. 4,897,252.

An improved process for the recovery of hydrogen peroxide from methyl benzyl alcohol oxidation mixtures is described in copending U.S. application Ser. No. 07/295,411 filed Jan. 10, 1989, U.S. Pat. No. 4,897,085.

During molecular oxygen oxidation of methyl benzyl alcohol to produce hydrogen peroxide with acetophenone as a coproduct, organic peroxidic materials such as ethyl benzene hydroperoxide (EBHP), cumine hydroperoxide, tertiary butyl hydroperoxide (TBHP) and ethyl benzene hydroxyhydroperoxide are formed. It is generally advantageous to separate the bulk of the hydrogen peroxide by water extraction from an organic phase which contains acetophenone and other organics. However, due to the distribution equilibrium between the organic and aqueous phases, a small amount of the hydrogen peroxide and the bulk of the organic peroxidic materials remain in the organic phase.

In certain preferred operations, the acetophenone in the organic phase is hydrogenated to methyl benzyl alcohol which can be recycled to the oxidizer or which can be converted to styrene monomer. For safety reasons as well as to avoid process difficulties such as catalyst deactivation, it is important to decompose active oxygen compounds associated with the acetophenone before further processing. It is also extremely important to ensure that active oxygen-containing compounds are selectively converted to acetophenone and methyl benzyl alcohol in order to avoid uneconomic $C_8$ yield losses.

For removal of trace amounts of $H_2O_2$ from the organic stream, various techniques are practiced in the commercial anthraquinone process for the manufacture of $H_2O_2$. It has been known, for example, that $H_2O_2$ can be catalytically decomposed by various heavy metals such as iron, nickel and copper or noble metals like platinum or palladium. The corresponding metal oxides and hydroxides also act in a similar manner. An essential drawback of this treatment is that the liberated oxygen reacts with hydroquinone present in the solution with renewed formation of $H_2O_2$. Also, in this practice, there is no emphasis given on enhancing the recovery of organic compounds which are recycled.

Treatment with solid substances or substances dissolved in water, which are capable of binding $H_2O_2$ such as sodium hydroxide, sodium metaborate or sodium carbonate has likewise been known. However, the efficiency of this treatment, which is often accompanied by a chemical change, is very low. It has also been suggested to treat organic solutions with mangano- and ferro-compounds, e.g. with a solution of $FeSO_4$ or with alcoholic solution or suspension which contains Fe-$(OH)_2$. However, apart from the consumption of chemicals, such procedures are not satisfactory because manganese or iron enters into the organic solution, and this results in decomposition in the oxidation step. U.S. Pat. No. 3,107,151 describes use of stannous salts like chloride, sulfate or fluoride for $H_2O_2$ decomposition. However, it makes the solution very acidic. U.S. Pat. No. 2,869,989 describes use of thermal treatment of the organic solution by using a distillation column. However, it is a complicated and capital intensive process.

The present invention provides a process for the selective decomposition of hydrogen peroxide and other active oxygen species in an organic stream such as that which results after separation of hydrogen peroxide from a methyl benzyl alcohol oxidate mixture.

SUMMARY OF THE INVENTION

In accordance with the invention, the organic stream containing active oxygen compounds is contacted at reactive conditions with an alumina catalyst for a time sufficient to substantially completely decompose the active oxygen constituents. In especially preferred practice, the alumina catalyst has associated therewith a noble metal such as palladium.

BRIEF DESCRIPTION OF THE DRAWING

The accompanying FIG. 1 illustrates in schematic form a suitable embodiment of the invention.

DETAILED DESCRIPTION OF THE INVENTION

Copending application Ser. No. 07/296,411 filed Jan. 10, 1989 provides an effective method for the recovery of hydrogen peroxide from methyl benzyl alcohol oxidate reaction mixtures.

In accordance with the process of application Ser. No. 07/295,411, a methyl benzyl alcohol oxidate mixture, which comprises methyl benzyl alcohol, acetophenone and hydrogen peroxide, is admixed with ethyl benzene solvent, and the resulting admixture is extracted with deionized water resulting in an organic phase comprised of the ethyl benzene extractive solvent, methyl benzyl alcohol and acetophenone; and an inorganic phase comprised of hydrogen peroxide in water.

It has now been found that the organic phase from such a separation contains very small but significant amounts of active oxygen-containing materials including hydrogen peroxide, methyl hydroperoxide, ethyl benzene hydroperoxide, ethyl benzene hydroxyhydroperoxide and the like. In accordance with the invention, the organic phase is contacted with an alumina catalyst at reactive conditions for a time sufficient to selectively decompose the active oxygen components, the organic active oxygen-containing materials selectively decomposing to acetophenone and methyl benzyl alcohol.

Alumina catalysts which are employed are solid materials comprised of at least 10 weight % $Al_2O_3$. Alpha alumina is suitable as are the silica alumina zeolites such as mortenite and the synthetic zeolites illustrated by Z5M-5 and analogous materials. Amorphous silica aluminas can be used.

It is especially advantageous to employ catalysts which comprise a noble metal such as platinum or palladium on an alumina support. Such catalysts are known commercially; one such catalyst is a 5 weight % Pd on alumina material. Generally, the noble metal will comprise 1–20 weight % of the catalyst composition.

Referring to the drawing, a methyl benzyl alcohol stream is introduced via line 101 into oxidation reactor 102. Most suitably, the methyl benzyl alcohol stream also comprises acetophenone and represents a process stream available from commercial propylene oxide/styrene monomer technology. Methyl benzyl alcohol is oxidized in reactor 102 by contact with molecular oxygen introduced as air via line 103. Conditions of the oxidation to form hydrogen peroxide and acetophenone are preferably as described in copending application Ser. No. 07/295,409 filed Jan. 10, 1989.

Liquid reaction mixture is withdrawn from reactor 102 via line 104 and comprises unreacted methyl benzyl alcohol, acetophenone oxidation coproduct as well as such acetophenone as may be present with the methyl benzyl alcohol feed, and hydrogen peroxide product.

Fresh ethyl benzene is introduced via line 105, and recycled ethyl benzene from ethyl benzene back extractor unit 112 is introduced via line 106 and combined with the oxidate mixture. The resulting admixture is passed to the bottom of $H_2O_2$ extractor 108. This light organic phase passes upwardly in 108, countercurrently contacting a heavy aqueous phase passing downwardly from the top, introduced by line 110. A large percentage of $H_2O_2$ contained in the organic feed is extracted into the aqueous stream which exits from below via line 109.

The organic phase, now with most of the $H_2O_2$ product removed, exits 108 from the top via line 111. Contained in this organic phase, as previously mentioned, are small but significant quantities of hydrogen peroxide and organic active oxygen compounds.

The organic phase passes via line 111 to zone 120 wherein it is contacted with the alumina catalyst at conditions whereby the active oxygen materials are substantially completely decomposed, the organic materials selectively decomposing to acetophenone and methyl benzyl alcohol. Generally, the contact is at 30° to 90° C. and 1–10 atmospheres, preferably 1–3 atmospheres for 5 to 90 minutes, preferably 15 to 45 minutes.

The mixture from zone 120 passes via line 121 to column 115 wherein it is distilled to separate ethyl benzene overhead via line 116 from the higher boiling methyl benzyl alcohol/acetophenone mixture which is removed via line 117. The ethyl benzene can be recycled to the extraction units or used elsewhere. The methyl benzyl alcohol/acetophenone is especially advantageously dehydrated in accordance with known procedures to form styrene monomer from the methyl benzyl alcohol, followed ultimately by hydrogenation of the acetophenone to produce more methyl benzyl alcohol.

The aqueous hydrogen peroxide phase removed from 108 is sent via line 109 to the top of ethyl benzene back extraction unit 112. The purpose of 112 is to remove and recover dissolved organics in stream 109 by countercurrent extraction with fresh ethyl benzene. The fresh ethyl benzene enters the bottom of extractor 112 via line 113 and travels upwards through the column. The organic product from 112 exits the top via line 106, and is recycled to the organic feed to $H_2O_2$ extractor 108. The purified aqueous hydrogen peroxide phase exits 112 via line 114. If desired, this stream can be treated by conventional procedures to further concentrate and purify the hydrogen peroxide product.

The following examples illustrate the invention. Unless otherwise indicated, parts are weights per hour and percentages are by weight.

EXAMPLE 1

100 grams of an organic product stream from the water extractor containing 31.6% methyl benzyl alcohol, 16.7% acetophenone, and 54.7% ethyl benzene, 1000 ppm $H_2O_2$, and 8788 ppm other active oxygen organic species (such as ethyl benzene hydroperoxide, tertiary butyl hydroperoxide, ethyl benzene hydroxyhydroperoxide and the like) was contacted with 8 grams of 5% Pd/Alumina catalyst from Engelhard at 38° C. for 15 minutes at atmospheric pressure. The solution was then filtered through a 0.2 micron filter paper and analyzed. Complete decomposition of $H_2O_2$ was observed (<25 ppm). Only 239 ppm of active oxygen organic species were found in the product sample. The concentration of methyl benzyl alcohol and acetophenone in the product sample was 34.6% and 18.4% respectively which indicates that the active oxygen organic species selectively decomposed to yield methyl benzyl alcohol and acetophenone.

EXAMPLE 2

In another experiment, 100 grams of organic product out of the water extraction unit containing about 36% methyl benzyl alcohol, 15.9% acetophenone, 35.3% ethyl benzene, 1.1% $H_2O_2$ and 0.64% other active oxygen species was contacted with 10 grams of Fisher alumina catalyst at 65° C. for 30 minutes at atmospheric pressure. The solution was then filtered through a 0.2 micron filter and analyzed. Once again complete decomposition of $H_2O_2$ was observed (<25 ppm). About 0.4% of active oxygen species were found in the product solution. Also, the amount of methyl benzyl alcohol and acetophenone in the product solution was higher (42.1% and 18.5% respectively) indicating decomposition of active oxygen organic species selectively to these materials.

What is claimed is:

1. The process wherein an organic stream containing hydrogen peroxide and organic active oxygen-containing compounds are contacted with an alumina catalyst at conditions whereby the said hydrogen peroxide and organic active oxygen compounds are decomposed, said organic active oxygen-containing compounds selectively decomposing to acetophenone and methyl benzyl alcohol.

2. The process wherein an organic stream containing hydrogen peroxide and organic active oxygen-containing compounds are contacted with an alumina catalyst comprising a noble metal supported on an alumina-containing carrier at conditions whereby the said hydrogen peroxide and organic active oxygen compounds are decomposed, said organic active oxygen-containing compounds selectively decomposing to acetophenone and methyl benzyl alcohol.

3. The process wherein an organic stream containing hydrogen peroxide and organic active oxygen-containing compounds are contacted with a palladium on alumina catalyst at conditions whereby the said hydrogen peroxide and organic active oxygen compounds are decomposed, said organic active oxygen-containing compounds selectively decomposing to acetophenone and methyl benzyl alcohol.

* * * * *